United States Patent [19]

Anderson

[11] 4,074,564

[45] Feb. 21, 1978

[54] RECONSTRUCTION SYSTEM AND METHOD FOR ULTRASONIC IMAGING

[75] Inventor: Weston A. Anderson, Palo Alto, Calif.

[73] Assignee: Varian Associates, Inc., Palo Alto, Calif.

[21] Appl. No.: 645,061

[22] Filed: Dec. 29, 1975

Related U.S. Application Data

[63] Continuation of Ser. No. 464,072, April 25, 1974, abandoned.

[51] Int. Cl.² ............................................. G01N 29/04
[52] U.S. Cl. ........................................ 73/596; 73/606; 73/609; 73/641
[58] Field of Search .................. 73/67.5 R, 67.6, 67.7, 73/67.8 R, 67.8 S, 67.9; 250/272, 312, 321, 358, 360, 264, 366; 340/5 MP

[56] References Cited

U.S. PATENT DOCUMENTS

| | | | |
|---|---|---|---|
| 2,612,772 | 10/1952 | McConnell | 73/67.5 R |
| 2,971,372 | 2/1961 | Lewis et al. | 73/67.5 R |
| 3,024,644 | 3/1962 | Fry et al. | 73/67.5 R |
| 3,052,115 | 9/1962 | Renaut et al. | 73/67.5 R |
| 3,673,394 | 6/1972 | Hartman | 250/312 X |
| 3,756,071 | 9/1973 | Dory | 73/67.8 R |
| 3,771,355 | 11/1973 | Sachs | 73/67.5 R |
| 3,778,614 | 12/1973 | Hounsfield | 250/362 |
| 3,857,052 | 12/1974 | Beller | 73/67.8 S X |

OTHER PUBLICATIONS

Young, D., Collecting and Processing Automatic Inspection Data, Ultrasonics, Jan. 1969, pp. 51-56.

Primary Examiner—Richard C. Queisser
Assistant Examiner—John P. Beauchamp
Attorney, Agent, or Firm—Stanley Z. Cole; John J. Morrissey; Peter J. Sgarbossa

[57] ABSTRACT

Short bursts of ultrasonic energy are directed through a three-dimensional specimen to determine the spatial distribution of those structures within the specimen capable of affecting the waveform of the energy. Transducers are placed in spaced positions about the periphery of the specimen to measure the affected parameters (such as attenuation and delay time) of the energy as a result of passing through the specimen along paths between the spaced transducers. The output signals containing this transit time and energy absorption information are retained in a data storage device. Through conventional programming techniques, a computer processes the data and calculates a velocity or absorption profile for each path. The profiles are collectively used to reconstruct two-dimensional or three-dimensional images of the specimen.

39 Claims, 4 Drawing Figures

RECONSTRUCTION SYSTEM AND METHOD FOR ULTRASONIC IMAGING

This is a continuation of application Ser. No. 464,072, filed Apr. 25, 1974 now abandoned.

FIELD OF THE INVENTION

This invention relates to ultrasonic imaging, and more particularly to imaging devices in which data from a series of transmission paths through the specimen are collectively assembled to provide an image.

BACKGROUND OF THE INVENTION

Heretofore, the fixed specimen technique has been employed to obtain transmission type images. The specimen is irradiated with ultrasonic energy, and a single acoustical transducer is systematically moved about the specimen in order to determine the amplitude and phase of the pulses transmitted through the specimen as a function of position. (See Applied Physics Letters 11, page 19, 1967, "Simulated Reference in a Coarsely Sampled Acoustical Hologram" by A. F. Metherell and H. M. El-Sum.) Alternatively, both the source transducer and the receiving transducer may be fixed and the specimen rotated to obtain transmission data at various angles through the object. G. N. Hounsfield describes a moving detector spaced from a cw X-ray source having a fixed specimen therebetween (see "Computerized Transverse Axial Scanning-Tomography" in the British Journal of Radiology, 46, pages 1016–1047, Dec. 1973). Transmission data from each detector are reconstructed into an image by a computer. These prior art techniques require close tolerance moving parts to provide the mechanical rotating or scanning.

Reflective imaging techniques have also been employed in the prior art. The reflective technique relies on changes of transmission impedance, which generate a series of reflected pulses spaced according to the depth of each reflecting layer within the specimen. These range pulses respond to impedance changes and do not yield information about the absorption coefficient or velocity coefficient within the specimen.

SUMMARY OF THE INVENTION

It is therefore an object of this invention to provide a pulsed energy imaging device and method for obtaining an improved image of the interior of a three-dimensional body.

It is a further object of this invention to provide a pulsed energy imaging device and method employing an electronic scanning mechanism without moving parts.

It is another object of this invention to provide a pulsed energy imaging system and method in which the resolution and/or contrast of the image is a function of a predetermined characteristic of the energy pulse.

It is yet another object of this invention to provide a pulsed energy imaging device and method which are rapid and nondestructive, and which have a higher resolution power than can be obtained with prior art techniques.

It is another object of this invention to provide a pulsed ultrasonic imaging device employing peripheral transducers which can both transmit and detect ultrasonic energy.

It is still another object of this invention to provide a pulsed ultrasonic energy imaging device in which the differential velocities of sound through the specimen provide the internal spatial relationship for the image.

Briefly, these and other objects are obtained by providing pulses of energy, a characteristic of which is affected by the interior regions of the specimen. The specimen is irradiated from a plurality of directions to cause transmission through the specimen along a plurality of internal paths. The energy is detected after transmission through the specimen, and compared with the pretransmission status to determine the effect of the specimen material. The results of the comparison for each path are collectively processed, and the interior spatial relationships between the specimen regions are mathematically reconstructed. The reconstruction is then imaged or displayed for viewing.

BRIEF DESCRIPTION OF THE DRAWING

Further objects and advantages of the present ultrasonic imaging technique and the operation of the peripheral transducers will become apparent from the following detailed description taken in conjunction with the drawing in which.

DESCRIPTION OF THE PREFERRED EMBODIMENTS

Figure 1:
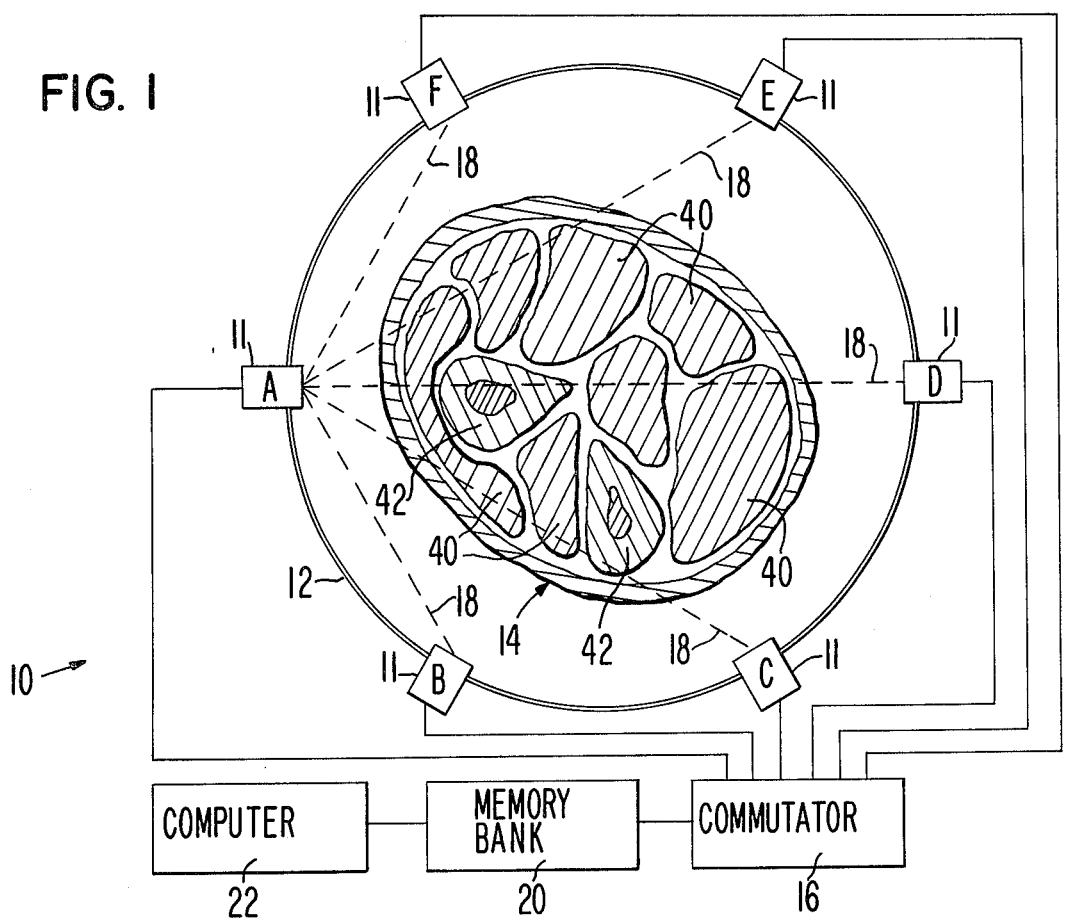
FIG. 1 is a sectional view of a patient's forearm showing a ring of peripheral ultrasonic transducers and associated processing apparatus.

FIG. 1 shows an ultrasonic imaging device 10 with a peripheral array 11 of six transducers A through F mounted on a ring assembly 12. The forearm of a patient is extended through ring 12 to the area to be examined, as indicated by cross-section 14. To insure good energy coupling between the transducers and the surface of the forearm, array 11 may be strapped around the forearm to establish direct contact, or the forearm and ring 12 may be submerged in water which has good acoustical transmission characteristics. Each transducer A through F may operate in either a transmission mode or a reception mode. The transducers transmit sequentially one at a time and receive simultaneously. That is, A transmits a short burst of ultrasonic energy into cross-section 14 which is detected by the remaining transducers B through F. Shortly thereafter, transducer B transmits a short burst of energy into cross-section 14, and the remaining transducers C through F and A detect the energy. This transmit-detect sequence is controlled by a commutator 16 or other suitable device for advancing the transmission position around ring 12 until each transducer has transmitted. The positions of transducers A through F determine the locations of paths 18 (shown by dotted lines in FIG. 1) through the specimen or cross-section 14. The total number N of specimen paths 18 between the various transducers A through F may be calculated by the formula:

$$N = \frac{n(n-1)}{2}$$

where $n$ is the number of transducers. The transmission and detection data for each specimen path are stored in a memory bank 20 and processed through a computer 22 which is programmed to reconstruct an image of the interior of the forearm cross-section 14.

Ultrasonic imaging device 10 is sensitive to the interior of a specimen having internal regions which differentially affect particular properties of ultrasonic energy. For example, regions having dense structures such as bone attenuate or absorb the ultrasonic energy pulses more than regions having other tissue structures such as muscle or fat. By comparing the pulse heights of the detected pulses, the different attenuation effects for each of the specimen paths may be determined and processed through a computer to reconstruct the original spatial relationship of the attenuating structures. Similarly, differential transmission rates (velocity) of the ultrasonic energy through the structure may be employed to reconstruct the image by determining the pulse delay across each of the specimen paths. For example, the velocity of ultrasound through blood is greater than through fat. Further, by varying the frequency of the ultrasonic energy in the input burst, several first derivatives with respect to frequency become available for further discrimination, i.e., $d$(attenuation)/$d$(frequency), and $d$(velocity)/$d$(frequency), and $d$(rise time change/$d$(frequency). Clearly, the imaging process may be based on any detectable waveform characteristics of the pulsed energy which the various tissue structures within the specimen differentially affect. The pulsing of the input energy introduces many parameters that can be monitored. The continuously operated X-ray device of G. N. Hounsfield is capable only of attenuation monitoring because the input energy is not in a pulse or periodic waveform.

Figure 2:
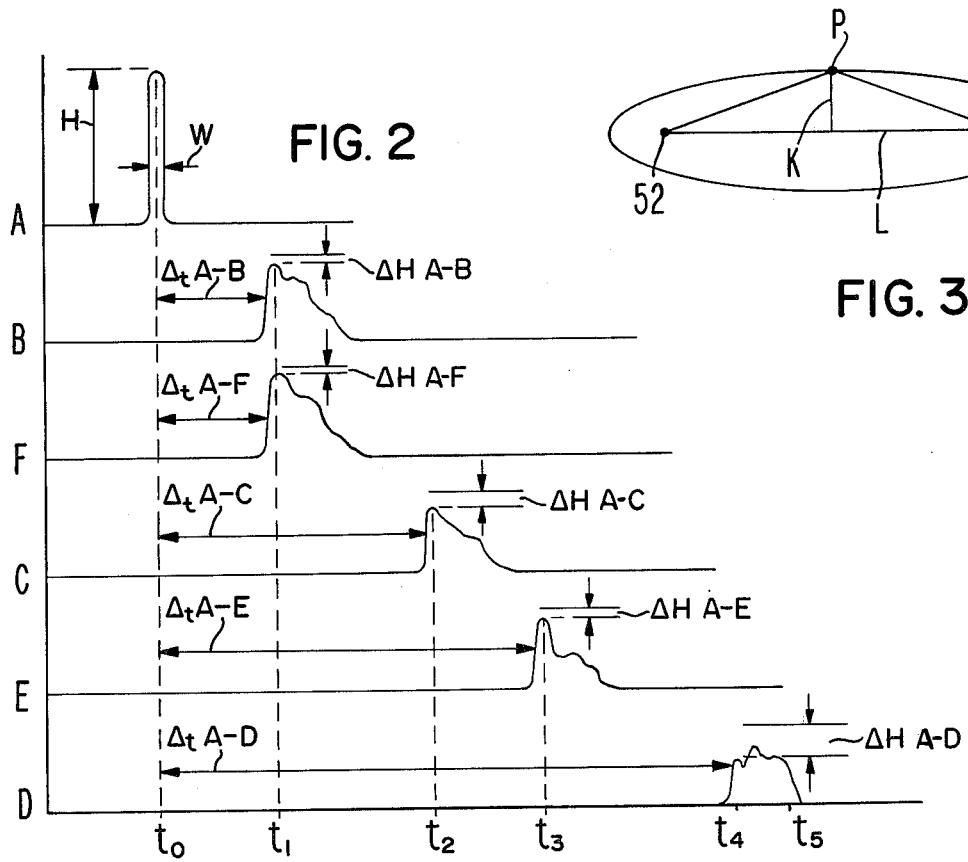
FIG. 2 is a graphic display of a transmitted ultrasonic pulse of FIG. 1 and the subsequent detected pulses, showing the time and amplitude relation therebetween.

FIG. 2 graphically depicts the pulsed energy transmitted from transducer A and the energy detected by transducers B through F. At time $t = 0$, a burst of ultrasonic is transmitted from transducer A. A pulse with a width of about one microsecond and peak pulse power of from about 10 mw to about 100 mw is suitable for the forearm application. Greater energies may be employed subject to the yet-to-be-determined effect of the heat thus transferred to the specimen. Also, lower energies may be employed subject to a diminishing signal-to-noise ratio.

The pulsed ultrasonic energy may be a short square wave pulse, an envelope of many cycles of short wavelength energy, or a half cycle of ultrasonic energy as shown in FIG. 2. Suitable frequencies for ultrasonic medical applications are 1 to 10 MHz. At less than 1 MHz, the resolution degrades because the energy wavelength in water is greater than 0.15 cm over the energy frequency in MHz. Above 10 MHz, energy absorption increases, making detection of the transmitted signals difficult in all but thin specimens.

The acoustical energy is transmitted from transducer A in a fan-like configuration through specimen 14 towards the opposite side of ring assembly 12 as shown in FIG. 1. At time $t_1$, the energy arrives at transducers B and F, which are adjacent to the transmitting transducer A and hence have the shortest transmission paths. In FIG. 1, paths A-B and A-F lie outside of forearm specimen 14, and hence the received energy is neither delayed nor attenuated in response to the tissue in forearm specimen 14. These two detected pulses contain no information about the interior of forearm specimen 14.

At time $t_2$, the energy is detected by transducer C. Path A-C passes through a muscular portion 40 and a bone portion 42 of forearm specimen 14 and is delayed and attenuated accordingly. At time $t_3$, slightly subsequent to time $t_2$, the transmitted burst arrives at transducer E. Path A-E is the same length as path A-C, but path A-E passes through muscular portion 40 only without passing through any bone material. The path A-C energy is attenuated substantially more than the path A-E energy, but is delayed less because ultrasonic energy has a higher velocity in bone than in muscle or fat.

Finally, at time $t_4$, the transmitted energy arrives at transducer D across path A-D which is the longest of the paths, causing the path A-D pulse to be the most attenuated. The transmission time and attenuation information indicated by the delta times and delta heights of FIG. 2 are stored in memory bank 20 of FIG. 1 along with similar information obtained by commutating the array and transmitting from the other transducers B through F. The density and absorption information about paths 18 is processed through computer 22 and an image of cross-section 14 is reconstructed.

Six transducers are employed in array 11 of FIG. 1 for simplicity of explanation. In actual practice, many more transducers would be employed to provide higher resolutions. Generally, higher resolutions are preferred because malfunctions may then be more accurately observed and diagnosed. A resolving power of about several millimeters is adequate to detect many masses and cysts of various kinds. Higher resolutions may be necessary for arterial clots, torn ligaments or bone fractures. A device suitable for the forearm application of FIG. 1 should have a resolution of about 2 millimeters, requiring about 250 transducers in peripheral array 11.

The greater the resolution required, the more transducers will be required on ring assembly 12, and the greater is the energy exposure time. The exposure time for a single transducer is typically one-half millisecond, and is determined by the transmission time of a particular path plus an echo subsidence time. A suitable pulse width is from 1 to 5 microseconds. A typical transmission time across a single path of 10 cm is approximately 70 microseconds. The time required for ultrasonic echoes to subside after detection is about 400 microseconds. Only a short period of perhaps 20 microseconds is required for electrical processing or commutation, which may overlap with the echo subsidence time. Thus, the total time required to operate a peripheral array of 250 transducers through one cycle is on the order of one-eighth of a second; and the exposure time for a 1000 transducer array is one-half second. The burden on the patient to hold his forearm still is very slight.

The information obtained from sequencing array 11 is used to produce an image of cross-section 14 shown in FIG. 1; that is, a two-dimensional image of a planar surface through the forearm. Three-dimensional images may be obtained by displacing ring assembly 12 longitudinally along the forearm specimen a millimeter or so depending on the resolution desired; and again commutating array 11. A series of the planar images may be assembled to reconstruct a three-dimensional image of the suspected region.

It is known that low levels of acoustical energy do not harm living tissue, as opposed to the damage frequently resulting from X-ray imaging or other high energy radiation techniques. Further, the present imaging system is based on propagation velocity, energy absorption, or some other parameter of transmission through the specimen. The transmission feature of the present technique permits imaging based on, for example, the velocity of sound through internal structures of the specimen. Various tissues are characterized by different sound velocities so that the technique permits tissue identification. Each differentially treated characteristic of the input pulse yields another possible mode of tissue discrimination. In contrast, the reflection technique indicates only the change of impedance along tissue interface, and a direct tissue characterization cannot be made.

Figure 3:
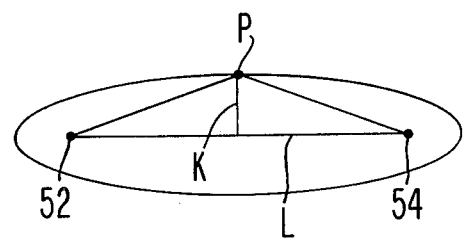
FIG. 3 shows the volume of space associated with one path between a particular pair of transducers.

FIG. 3 illustrates the principle that by accurately determining the first arrival time of a signal transmitted from a source 52 to a detector 54, one can insure that only the part of the object within the interior of an ellipsoid of revolution about points 52 and 54 will contribute to the time delay of the transmitted signal. An uncertainty, delta $t$, in the arrival time of a transmitted pulse causes some uncertainty in the velocity coefficient as well as an uncertainty in the path of the transmitted sound wave. The uncertainty of the path is determined by comparing the direct transmission time from source 52 to point P and thence to detector 54. For a given time uncertainty, delta $t$, the maximum displacement K of point P from the straight line path L between source 52 and detector 54 occurs when P is equidistant therebetween. An estimate of the maximum displacement K is made by setting the difference between direct and indirect travel time equal to the time uncertainty, delta $t$. Thus for a velocity of propagation C $$\Delta t = \frac{2}{C} \sqrt{\left(\frac{L}{2}\right)^2 + K^2} - \frac{L}{C};$$

and with the power series approximation $4K^2 << L^2$, this time uncertainty becomes $$\Delta t \cong \frac{2K^2}{CL}.$$

For the purposes of this approximation the sound velocity is assumed constant even though its value will depend upon position. The above equation is useful for estimating the time resolution, delta $t$, necessary to achieve a given spatial resolution K. For example, for a path length L = 100 mm, a velocity of propagation C = 1.5 mm/microsecond and a resolution K less than 3.0 mm required that delta $t$ be less than 0.24 microsecond.

An ellipsoid of revolution passing through point P with one focus at source 52 and the other focus at detector 54 has the property that the path length formed by two straight lines, one from one focus to a surface point and the other from the same surface point to the other focus, is a constant value independent of the particular surface point.

Figure 4:
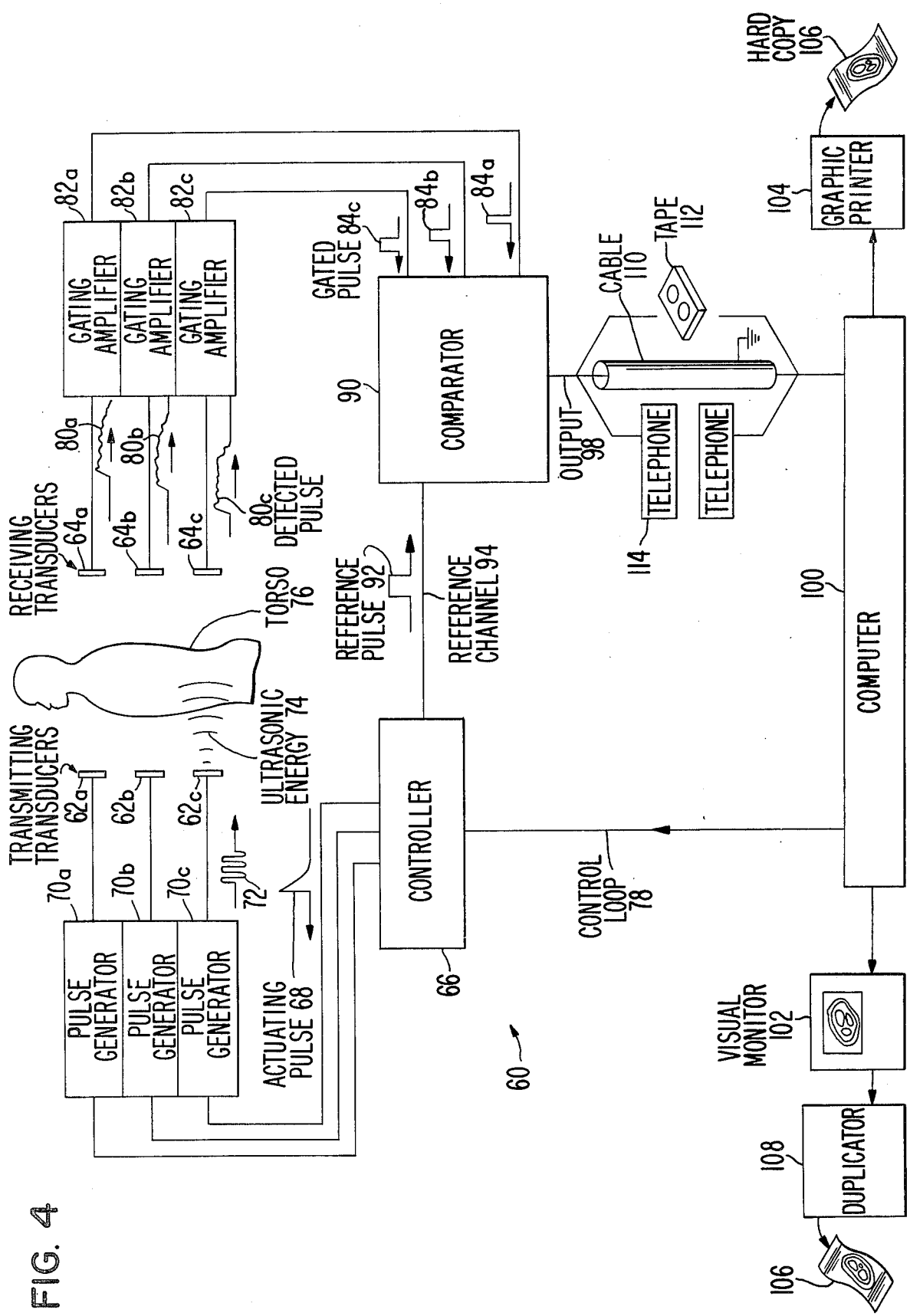
FIG. 4 is a block diagram of a complete ultrasonic imaging system with visual monitor and hard copy facilities.

FIG. 4 shows a complete reconstruction system 60 from the specimen to a visual monitoring and hard copy printout. For illustrative convenience, only three transmission transducers 62a, 62b, and 62c, and three receiving transducers 64a, 64b, and 64c, are shown. In actual practice, hundreds or even thousands of transducers may be employed. A controller 66 initiates the operation of reconstruction system 60 by providing an activating pulse 68 to one of a series of pulse generators 70a through 70c, 70c for instance, which in turn applies a sharp pulse of direct current or a few cycles of r.f. energy 72 to the associated transmission transducer 62c. Transmission transducer 62c converts energy pulse 72 into a short burst of ultrasonic energy 74 which is transmitted through an object to be imaged, such as torso 76. Controller 66 systematically activates all of the pulse generators 70 according to a standard format, or in response to a programmed computer through a control loop 78, to scan object 76. Controller 66 may activate pulse generators 70 sequentially in order of their physical position around specimen 76, or in any order desired. A pulse 72 with peak of about 1 watt is suitable to operate conventional ultrasonic transducers such as a crystal of lead zirconate titanate (PZT) one quarter inch in diameter made by the Clevile Corporation, or lead metaniobate made by Gulton Industries.

Ultrasonic pulse 74 spreads as it passes through specimen 76 and impinges separately on each of the three receiving transducers 64a, 64b, and 64c where it is converted back into electrical energy as detected pulses 80a, 80b and 80c. Detected pulses 80 are sequentially displaced in time. The receiving transducer closest to the energized transmission transducer is the first to generate a detected pulse 80. Detected pulses 80a, 80b and 80c are amplified by gating amplifiers 82a, 82b and 82c which preferably cut off the trailing portions thereof containing echo and reflected energy components, and pass only the leading portion of 84a, 84b and 84c. The leading portions of detected pulses 80a, 80b, and 80c contain the primary attenuation, delay, and rise time data that relate to the absorption, velocity and frequency dispersion of ultrasonic energy through specimen 76.

A comparator 90 receives gated pulses 84a, 84b, and 84c and systematically compares them to a reference pulse 92 forwarded from controller 66 to comparator 90 through a reference channel 94. Reference pulse 92 may be calibrated to account for reproduction imperfections inherent in transducers 62 and 64. Comparator 90 determines the changes in the magnitude, time, waveshape, phase, etc., of gated pulses 84, and reduces the primary data contained in pulses 84 into analog or digital data appearing at comparator output 98. Comparator 90 communicates the comparator output data to a computer 100 for reconstruction into a visible image. The reconstruction information may be organized for input to a visual monitor 102 such as a cathode ray tube, or for input into a graphic printer 104 such as an electrostatic stylus printer for providing a hard copy 106 of the reconstructed image. Alternatively, hard copy 106 may be obtained from visual monitor 102 through a duplicator 108.

Comparator output 98 may be directly linked to computer 100 by means of electrical connector or cable 110 or through a variety of other mediums such as magnetic tape cassettes 112 and telephones 114, for example. The bit packing density of tape 112 or the bit handling rate of telephone 114 may be accommodated by controlling the scan rate of controller 66.

The reconstruction of linear absorption data 96 into a two-dimensional or three-dimensional image may be accomplished by any of several computer programming techniques such as: The "Least Squares" technique described in "Three-Dimensional Density Reconstructions from a Series of Two-Dimensional Projections" by M. Gautier appearing in Nuclear Instruments and Methods, Vol. 101, pages 509–518 (1972); or the "Convolution" technique described in "Inversion of Fan- Beam Scans in Radio Astronomy" by R. N. Bracewell and A. C. Middle appearing in Astrophysical Journal, Vol. 150, pages 427–434 (1967), or the "Fourier Transform" technique in "The Effects of Incomplete Resolution on Surface Distributions Derived from Strip-Scanning Observations with Particular Reference to an Application in Radio Astronomy" by S. F. Smerd and J. P. Wild appearing in Philosophical Magazine, Series 8, 2, pages 119–130 (1957); or the "Algebraic Reconstruction" technique in "Algebraic Reconstruction Techniques (ART) for Three-Dimensional Electron Microscopy and X-ray Photography" appearing in the *Journal of Theoretical Biology*, Vol. 29, pages 471–481 (1970).

The objects of this invention have been achieved by employing a stationary annular transducer array which encompasses the specimen. The array is electrically commutated to pass pulses of short wavelength energy through the specimen at many angles along many different intersecting paths, thus eliminating the problem of mechanical registration as the angle advances. The transmission data from each angle are processed through a computer which mathematically reconstructs the interior spatial relationships of the various regions within the specimen. The pulsed or periodic nature of the input energy provides many waveshape parameters that may be monitored to increase the discrimination power of the array.

It will be apparent to those skilled in the art that various changes may be made in the apparatus and technique described without departing from the scope of the invention. Accordingly, the scope of the invention should be determined only by the wording of the following claims and their legal equivalents.

I claim as my invention:

1. In an image reconstruction apparatus for passing ultrasonic energy pulses through a specimen having regions which differentially affect particular features of the pulsed energy transmitted therethrough, the combination comprising:
   a plurality of ultrasonic energy transducers positioned about the periphery of said specimen;
   pulse generating means connectable to said transducers for providing pulses of ultrasonic energy having at least one predetermined feature, which pulses pass through the specimen along a plurality of intersecting paths;
   receiving means connectable to said transducers for detecting the pulsed energy subsequent to passing through the specimen;
   commutator means connecting said pulses generating means and said receiving means with said transducers, so that each transducer can be sequentially activated to transmit an ultrasonic energy pulse along a plurality of paths through said specimen to the other transducers connected as receivers to detect said pulse;
   comparing means for comparing the provided pulsed energy to the detected energy to determine comparison data; and
   computer means programmed to process the comparison data and reconstruct an image of the specimen.

2. The apparatus of claim 1 additionally comprising data storage means for storing the comparison data.

3. The apparatus of claim 1 additionally comprising graphic display means for viewing the reconstructed image.

4. The apparatus of claim 1 wherein the provided pulsed energy has a predetermined waveform responsive to the specimen regions, and the comparing means compares the first portion of the waveform of the provided energy with the first portion of the waveform of the detected energy.

5. The apparatus of claim 4 wherein the comparing means determines the delay time between the provided energy and the detected energy.

6. The apparatus of claim 4 wherein the comparing means determines the attenuation of the provided energy in passing through said specimen.

7. The apparatus of claim 4 wherein the comparing means determines the rise time change between the provided energy and the detected energy.

8. The apparatus of claim 4 wherein the provided pulsed energy is an envelope of many cycles of higher frequency ultrasonic energy pulses.

9. The apparatus of claim 4 wherein the wavelength of the provided energy pulses is variable, and the comparing means detects the first derivative of said predetermined feature with respect to frequency, i.e., $d$(predetermined feature)$/d$(frequency).

10. The apparatus of claim 9 wherein the comparing means detects the first derivative with respect to frequency of the delay time between said provided energy and said detected energy, i.e., $d$(delay time)$/d$(frequency).

11. The apparatus of claim 9 wherein the comparing means detects the first derivative with respect to frequency of the attenuation of said provided energy in passing through said specimen, i.e., $d$(attenuation)$d$(frequency).

12. The apparatus of claim 9 wherein the comparing means detects the first derivative with respect to frequency of the rise time change between said provided energy and said detected energy, i.e., $d$(rise time change)$/d$(frequency).

13. A method of reconstructing an image of the interior of a specimen having regions therein which differentially affect particular features of pulses of ultrasonic energy transmitted therethrough, said method comprising the steps of:
   irradiating the specimen with ultrasonic energy pulses causing transmission thereof along a plurality of intersecting paths through each region of said specimen, said pulses having at least one predetermined feature;
   detecting the energy pulses after being transmitted through the specimen;
   determining for each of said plurality of paths any change which occurs in one or more predetermined features of the energy pulses as a result of being transmitted through the specimen including the time delay imposed thereby;
   mathematically reconstructing the spatial relationships between the regions within the specimen by utilizing information including said time delay for each of said plurality of paths; and
   providing an image of the interior of the system from the reconstruction of said spatial relationships.

14. The method of claim 13 wherein the plurality of paths through the specimen are substantially coplanar, and the image provided is a two-dimensional image of the plane through the specimen defined by the coplanar paths.

15. The method of claim 14 comprising the additional step of irradiating the specimen along a plurality of sets of coplanar paths, each set of which defines a plane displaced from the plane defined by any other set of coplanar paths, to provide three-dimensional data of the specimen for the reconstruction and imaging steps.

16. The method of claim 13 wherein only the first portion of the ultrasonic energy pulses are used in determining any change in a predetermined feature of said pulses.

17. An apparatus for reconstructing an image of the internal structure of a specimen having regions which differentially affect particular features of ultrasonic energy pulses transmitted therethrough, said apparatus comprising:
source means for transmitting ultrasonic energy pulses along a plurality of intersecting paths through each region of said specimen, said pulses having at least one predetermined feature,
receiving means for detecting said energy pulses subsequent to the passage of said pulses through said specimen,
comparison means for comparing the transmitted pulses to the detected pulses for generating comparison data for said plurality of paths, including information as to the time delay imposed upon said transmitted pulses by passage through said sample; and
computer means programmed to process said comparison data including said time delay information for said plurality of paths to reconstruct an image of the specimen therefrom.

18. The apparatus of claim 17 further comprising data storage means for storing said comparison data.

19. The apparatus of claim 17 further comprising graphic display means for viewing the reconstructed image.

20. The apparatus of claim 17 wherein the transmitted energy pulses have a predetermined initial pulse shape, the subsequent pulse shape of said pulses being changeable in response to said regions within said specimen as said pulses propagate through said regions, and wherein said comparison means compares the first portion of the initial pulse shape of each transmitted pulse with the first portion of the corresponding pulse shape as detected by said receiving means.

21. The apparatus of claim 20 wherein said comparison means determines the delay time betwen said first portion of the initial pulse shape of each transmitted pulse with the first portion of the pulse shape of each corresponding detected pulse.

22. The apparatus of claim 20 wherein said comparison means determines the attenuation of said transmitted energy in passing through said specimen.

23. The apparatus of claim 20 wherein said comparison means determines the rise time change between said transmitted pulses and said corresponding detected pulses.

24. The apparatus of claim 20 wherein each of said transmitted pulses is an envelope of many cycles of higher frequency ultrasonic energy pulses.

25. The apparatus of claim 24 wherein the wavelength of said transmitted pulses is controlledly variable, and said comparison means detects the first derivative with respect to frequency of said predetermined feature of said pulses.

26. The apparatus of claim 25 wherein said comparison means detects the first derivative with respect to frequency of the delay time between said transmitted pulses and said corresponding detected pulses.

27. The apparatus of claim 25 wherein said comparison means detects the first derivative with respect to frequency of the attenuation of said transmitted energy in passing through said regions.

28. The apparatus of claim 25 wherein said comparison means detects the first derivative with respect to frequency of the rise time change between said transmitted pulses and said corresponding detected pulses.

29. The apparatus of claim 17 wherein said source means comprises a plurality of ultrasonic energy transducers positioned about the periphery of said specimen.

30. The apparatus of claim 29 wherein at least some of said ultrasonic energy transducers also convert ultrasonic energy into electrical energy.

31. The apparatus of claim 30 further comprising commutator means for sequentially activating each one of said plurality of ultrasonic energy transducers to transmit ultrasonic energy on a plurality of paths through said specimen.

32. A method of reconstructing an image of the interior of a specimen having regions therein which differentially affect the velocity of pulses of energy transmitted therethrough, said method comprising the steps of:
irradiating the specimen with energy pulses, causing transmission thereof along a plurality of intersecting paths through each region of said specimen;
detecting the energy pulses after being transmitted through the specimen;
determining the time delay which occurs as a result of the pulses being transmitted through the specimen; and
mathematically reconstructing the differential velocity coefficients for the regions which differentially affect the velocity of the pulses transmitted through the specimen to provide an image of the internal spatial relationships within said specimen.

33. An apparatus for reconstructing an image of the internal structure of a specimen having regions which differentially affect the velocity of energy pulses transmitted therethrough, said apparatus comprising:
source means for transmitting energy pulses along a plurality of intersecting paths through each region of said specimen;
receiving means for detecting said energy pulses subsequent to the passage of said pulses through said specimen;
means for determining the time delay of the transmitted pulses in passing through said specimen, and for generating delay data; and
computer means programmed to process said delay data to reconstruct an image of said specimen.

34. A method as in claim 32 in which said irradiating is accomplished by means of a plurality of energy transmitters positioned about the periphery of said specimen, each directing said pulses of energy along one of said plurality of said intersecting paths.

35. A method as in claim 32 in which said irradiating is accomplished by means of at least one ultrasonic transducer.

36. An apparatus as in claim 33 in which said source means comprise a plurality of energy transmitters positioned about the periphery of said specimen, each directing said pulses along one of said plurality of said intersecting paths.

37. An apparatus as in claim 33, in which said source means comprises at least one ultrasonic transducer.

38. In an image reconstruction apparatus for passing ultrasonic energy pulses through a specimen having regions which differentially affect particular features of the pulsed energy transmitted therethrough, the combination comprising:
- a plurality of ultrasonic energy transducers positioned about the periphery of said specimen for directing the transmission of ultrasonic energy therethrough along a plurality of intersecting paths, and for detecting the pulsed energy subsequent to passing through the specimen along said intersecting paths;
- pulse generating means connectable to said transducers to enable transmission of said ultrasonic energy in pulses having at least one predetermined feature;
- comparing means for comparing the provided pulsed energy to the detected energy to determine comparison data; and for said plurality of paths, including information as to the time delay imposed upon said transmitted pulses by passage through said specimen
- computer means programmed to process the comparison data including said time delay information for said plurality of paths and reconstruct an image of the specimen.

39. The apparatus of claim 38 which further includes means for connecting said transducers and said pulse generating means to transmit means to transmit pulsed energy along said plurality of intersecting paths, and to connect said transducers to detect said pulsed energy subsequent to passing through said specimen.

* * * * *